United States Patent [19]

Kranz et al.

[11] Patent Number: 4,842,606

[45] Date of Patent: Jun. 27, 1989

[54] BONE IMPLANT

[75] Inventors: Curt Kranz, Berlin; Amir Zahedi, Münster; Emmanuel Anapliotis, Berlin, all of Fed. Rep. of Germany

[73] Assignee: Mecron Medizinische Produkte GmbH, Berlin, Fed. Rep. of Germany

[21] Appl. No.: 26,320

[22] Filed: Mar. 16, 1987

[30] Foreign Application Priority Data

Mar. 15, 1986 [DE] Fed. Rep. of Germany ....... 3609121
Jul. 29, 1986 [DE] Fed. Rep. of Germany ....... 3625520

[51] Int. Cl.$^4$ ............................................... A61F 2/32
[52] U.S. Cl. ........................................... 623/23; 623/18
[58] Field of Search ................. 623/16, 20, 18, 22, 623/23

[56] References Cited

U.S. PATENT DOCUMENTS

| | | |
|---|---|---|
| 3,102,536 | 9/1963 | Rose et al. ............... 623/23 |
| 3,889,299 | 6/1975 | Osborne ................... 3/1 |
| 3,903,549 | 9/1975 | Deyerle .................. 3/1.912 |
| 3,974,527 | 8/1976 | Shersher ................. 3/1.912 |
| 3,990,117 | 11/1976 | Pritchard et al. ........ 623/20 |
| 4,123,806 | 11/1978 | Amstutz et al. .......... 3/1.912 |
| 4,224,698 | 9/1980 | Hopson .................. 3/1.912 |
| 4,257,129 | 3/1981 | Volz .................... 623/20 |
| 4,310,931 | 1/1982 | Muller .................. 3/1.913 |
| 4,404,692 | 9/1983 | Eftekhar ................ 3/1.912 |
| 4,532,611 | 8/1985 | Halpern ................. 623/23 |
| 4,536,894 | 8/1985 | Galante et al. .......... 623/16 |
| 4,619,569 | 10/1986 | Wright .................. 623/23 |
| 4,645,506 | 2/1987 | Link .................... 623/23 |
| 4,657,551 | 4/1987 | Ecke .................... 623/23 |
| 4,666,450 | 5/1987 | Kenna ................... 623/22 |
| 4,681,590 | 7/1987 | Tansey .................. 623/23 |
| 4,704,128 | 11/1987 | Frey .................... 623/23 |

FOREIGN PATENT DOCUMENTS

| | | | |
|---|---|---|---|
| 2530254 | 10/1980 | Fed. Rep. of Germany | 623/23 |
| 0557676 | 1/1975 | Switzerland | 623/20 |
| 2142830 | 1/1985 | United Kingdom | 623/23 |
| 2153233 | 8/1985 | United Kingdom | 623/23 |

OTHER PUBLICATIONS

Brown et al., "A Contact-Coupled Finite Element Analysis of the Natural Adult Hip," 17, J. Biomechanics, 437-448 (1984).

Primary Examiner—Richard J. Apley
Assistant Examiner—D. Isabella
Attorney, Agent, or Firm—Spencer & Frank

[57] ABSTRACT

A bone implant, in particular as a shaft-type prosthesis, which has a mirror-symmetrical shape is proposed, wherein for adaptation to bone regions of the left or right half of the body that in themselves are not mirror-symmetrical, the part having mirror-symmetrical shape forms a basic element, and a separately shaped additional element is provided that is joined or can be joined to the basic element in such a manner that a bone implant that is not mirror-symmetrical and is usable only on the left or right side of the body is produced.

16 Claims, 3 Drawing Sheets

BONE IMPLANT

BACKGROUND OF THE INVENTION

The invention relates to a bone implant

Bone implants of this kind are known, for example in the form of hip joint prostheses, which are suitable for implantation on both sides of the body. For especially adapting to the different shape of the parts of the bones on the left and right sides of the body, special prostheses are produced in each case, with an overall shape that from the outset is adapted to one or the other of the halves of the body.

SUMMARY OF THE INVENTION

In a bone implant of the aforementioned type, the object of the invention is to enable simplified and less expensive production, by providing that the basic shape, which entails the greatest production cost, can be embodied identically for both halves of the body.

The invention is based on the recognition that a non-mirror-symmetrical bone implant, in particular a shaft for a femoral hip joint prosthesis, can be broken down into mirror-symmetrical component parts plus at least one additional element that can be attached later.

By providing for different sizes of the additional elements, even more-individualized tailoring to the anatomy can be obtained. With connection surfaces provided on facing sides of the basic element of the implant, or fastenening means for the additional elements, an implant for the left-hand or righthand side of the body can be prepared as desired, using only one basic element and the appropriate additional, element.

The selective fastenening of two attachments, which provide the tailoring to the shape of the bone of the particular half of the body, is attained ina simple monner by providing that in the vicinity of two facing surfaces, the basic element has fastening means accessible from outside for anchoring the additional element. Because the fastening means provided are let into the outer contour in a recessed manner, the side of the implant not having an additional elements are disposed symmetrically with a surface (plane of symmetry) dividing the basic element into two mirror-symmetrical halves, then the additional elements for use in the left or right half of the body can also be embodied symmetrically with respect to one another and are therefore simple to manufacture by making slight changes in the machine tools.

Another favorable feature of the invention is that the additional elements are embodied in such a way that they too are mirror-symmetrical. The symmetry in that case is in terms of the plan view, that is, viewed toward the connection surface of the implant. The plane of symmetry that is, the imaginary mirror — thus forms a face extending at right angles to the connection surface of the implant. Only a single additional element is then required to both halves of the body.

The symmetrical shape is substantially brought about by the (imaginary) superimposition of the two non-symmetrical shapes, in such a manner that the region in space in which both parts intersect forms the symmetrical shape. As a result, non-symmetry in the vicinity of the connection face with respect to the basic element is not precluded, because this face can be embodied freely — on the condition that the opposing face has a corresponding shape.

If the recess through the implant is embodied as a continuous bore or as some other (prismatic) opening, then it is simple to produce, because in that case both sides of the implant can be machined in a single operation. With symmetrical embodiment of the additional element, the opening is preferably made symmetrical as well, because in that case the same profile can be used for its entire length.

In the different variants, at least one recess is produced, in the form of a bore or slit or as a groove extending along the surface, which provides a subsantial opportunity for engagement of the retaining element, for anchoring the fastening element. In the case of dovetail-like recesses, the additional element can be pushed in, while in the case of other shapes of recess having a cylindrical or other prismatic form the additional element is embodied such that it is insertable.

The fastening direction, that is the direction in which the additional elements are inserted, in the case of shaft prostheses or other implants that are drivable into the bone is crosswise or in the opposite direction from the driving-in direction, that is, in particular crosswise or opposed to the shaft direction, so that there need be no fear that it will loosen, even when driving in is performed with great force.

The fastening of the additional element in the recess is improved by the provision that the recess tapers toward the surface at which the additional element can be jouined; with a recess shaped in continuous fashion, the tapering regions adjoin one another, so that the resultant bore as a whole is barrel-shaped or has a waist, that is, it is preferably likewise symmetrical to the plane of symmetry of the basic element. The additional element correcpondingly has a retaining element engaging the recess and widening toward the basic element, preferably also engaging undercuts or elastically snapping into a detent with the undercuts. If the additional element of the bone implant, then by selection of a the basic element of the bone implant, then by selection of a suitable additional element the implant can be completed in a simple and rapid manner with the selected additional element.

Even if the recess is purely cylindrical or prismatic and continuous, spreadable extensions assure good adhesion. For spreading the extensions - and thus for durable fastening of the additional element — a wedge or truncated wedge that can be snapped into a detent between the extensions is introduced in the same direction as or in the opposite direction from the save direction as ar in the opposite direction from the insertion direction of the additional element, and this wedge remains between the extensions and spreads them apart permanently. The extensions of the additional element are in particular formed by dowel-like fastenings into which a wedge pin or a wedge bolt, as a clamping element, and in particular having a conical shaft or head can be introduced for locking purposes.

To attain good matching of the implant to the interior of the bone, and in particular to attain a firmly seated contact over a large surface area, it is favorable for the additional element to be embodied as resilient, in particular elastic, in the direction toward the basic element, the resiliency being generatable by recesses or corrugation of the three-dimensionally deformed metal sheet forming the additional element. Because the additional element has a three-dimensional deformation in the sense of a height that distances it substantially from the basic element, the resiliency can be much greater than in the case of implants containing inserted sheet-metal parts that extend parallel to the surface of the basic element and do not at the same time provide a three-dimensional adaptation.

If the additional element has a surface structure that promotes connection with the adjoining region of the bone by promoting ingrowth, and this structure has regions with depressions that are filled with resorbable material, which is replaced with bane material after the implantation, then the implant can be introduced easily at first, because of its smooth surface, while afterward, by replacement of the resorbable material with bone material, an intimate joining of the implant surface with the surrounding bone is attained.

In an advantageous further feature of the invention, the additional element comprises three-dimensionally shaped sheet metal, which surrounds a cavity.

If the cavity has an access opening that is disposed on a part that is located toward the rear, with respect to the direction of introduction when the implant is put into place, then during the implantation bone chips can be introduced into the cavity through the access opening, and these bone chips promote "taking" of the implant. This access opening is preferably disposed on a part located toward the rear, with respect to the direction of introduction when the implant is put into place, so that even after the prosthesis has been inserted into the implantation area, the access opening will still be accessible.

To improve the connection of an implant with the adjoining bone regions, and in particular to improve "taking" of the implant, it is known to provide the surface of the implant with a textured structure. This texturing is initially produced by a corresponding shaping of the surface of the basic element itself (roughening by subsequent surface treatment, profiling when shaping the basic element, milling of slots, or the like). As noted, with implants that are of metal, this texturing is variously also generated by metal overlays or inlays in the form of perforated plates or wire cloth — which optionally may be partly embedded in the basic element — and which may be connected to the basic element. In the implant according to the invention, the surface texturing can favorably be provided simply on the additional element, so that by selecting a suitable additional element, the selection of a suitable surface structure can also be accomplished.

It will be appreciated that both the resiliency and/or elasticity and the surface texture — that is, the properties effecting a secure hold in the bone — can be united in the additional element, because this element forms a raised region that deviates proportionately the most from the basic shape. By purposeful selection of the shape and properties of this region, the seating and retention properties of the implant can be varied to the greatest possible extent, so that while keeping the same basic element, the desired properties of the implant can be varied over a wide range, by localized adaptation via the selection of a suitable additional element, with low material and storage costs.

For improved engagement with the surface of the bone, it is optionally also favorable for the additional element to have ribs or rib elements extending in the driving-in direction. Here again manufacture is simplified if the ribs or rib elements are located exclusively on the additional part, where they are particularly effective as retaining and guiding elements. In that case no ribs need to be generated on the mirror-symmetrical basic element. Here the additional part can again be produced in different variants, so that depending on the size of the bone to be provided with the bone implant, a fitting additional element can be fastened to the mirror-symmetrical basic component of the bone implant. The additional element preferably has ribs or rib elements that extend in the driving-in direction, and production is simplified if the ribs or rib elements are located exclusively on the additional part, where they are particularly effective as retaining and guiding elements.

Contrarily, the additional part can likewise be produced in different variants, so that depending on the size of the bone to be provided with the bone implant, a fitting additional element can be fastened to the mirror-symmetrical basic component of the bone implant.

The invention is preferably applicable to shaft-type prostheses for long bones, such as femur prostheses, and the additional element extends in a plane that is oriented parallel to the plane in which the shaft has its maximum curvature. By three-dimensional adaptation of this zone, the seating properties of femur prostheses can be tailored to indiviual patients and optionally varied further even during the operation.

Advantageous further developments of the invention are defined by the dependent claims and described below in further detail in terms of the preferred embodiments of the invention, referring to the drawings.

DESCRIPTION OF THE PREFERRED EMBODIMENTS

The exemplary embodiment of an implant according to the invention, in the form of a hip joint prosthesis, shown in the drawings (referring to FIGS. 1 and 2 initially), comprises a shaft 1, a neck 2 and a spherical articular head 3, the articular head being interchangeable by means of a cone connection. These elements form the mirror-symmetrical components of the hip joint prosthesis, and the shaft corresponds to the basic element mentioned above.

The hip joint prosthesis shown also has an additional element 4, which can be attached later, having ribs that extend in the driving-in direction, that is, in the direction of the longitudinal axis of the shaft. In the case of a hip joint prosthesis for the other side of the body, an additional element shaped mirror-symmethrically to that shown is selectively attached to the opposite side of the shaft according to FIG. 2.

Figure 3:
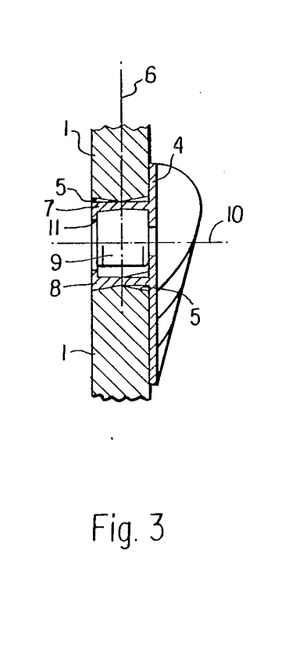
FIG. 3 is a sectional view of the detail III of the exemplary embodiment of FIG. 2, shown on a larger scale.

As FIG. 3 shows, an opening 5 in the form of a continuous bore is provided in the shaft 1, to serve as a recess for receiving a fastening element of the additional element 4. The bore tapers toward the middle, so that a spreading fastening element for an additional element provided on the opposite side gains a hold in the associated conical region and can be fastened in a simple manner by means of a dowel-like element. The basis element can also be implanted without an additional element, because there are no protruding parts to present problems. The opening 5 extends mirror-symmetrically with respect to the plane of symmetry 6. The additional element 4 is inserted into this opening by means of two integrally formed-on extensions 7 and 8. The free ends of the extensions 7 and 8 can be spread apart in such a way that they grasp the narrowest portion (waist) of the opeining 5, located in the plane of symmetry, from behind. By means of a central bore as a recess, they form a kind of dowel, which is lent its retaining force by a spreading element 9 driven in there, the bore being adapted to this element 9. The extension 8 is shown in the spread-apart state, which is compelled by means of a truncated wedge 9, as the spreading element, that is driven in (from the left as seen in the drawing), only the part located below the center line 10 being shown in the drawing. The upper half is left out, so as to show the view into the opening 5 in the shaft 1 of the situation immediately following the introduction of the additional element 4.

The extension 7 has a thickened portion 11 on its free ends, which prevents a driven-in truncated wedge from sliding back out of the region of the hole. In this manner a clamping connection is produced, with the aid of which the additional element 4 can be fastened durably to the shaft 1. It will be appreciated that the extensions 7 and 8 can be embodiment in such a way that they have attachments that after the introduction engage undercuts of the bores. In that case, instead of the conical regions, corresponding stepped zones should be provided.

It will be appreciated that clamping or wedging of the additional element can be done in a various ways; the recess of the basic elements can be kept relatively smooth in its walls, and the retaining element (extensions) can at first simply snap into place after being manually pressed in. The spreading or clamping element then acts as the locking and securing means, even under the forces arising with relatively great strain.

Figures 1, 6:
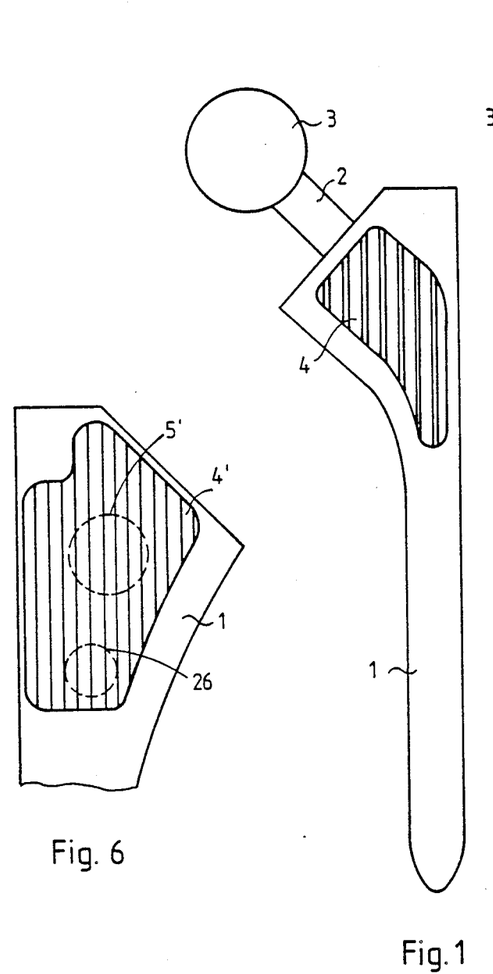
FIG. 1 is a side view of an exemplary embodiment of the implant according to the invention, in the form of a hip joint prosthesis.
FIG. 6 is a side view of the variant according to FIG. 4.
Figure 2:
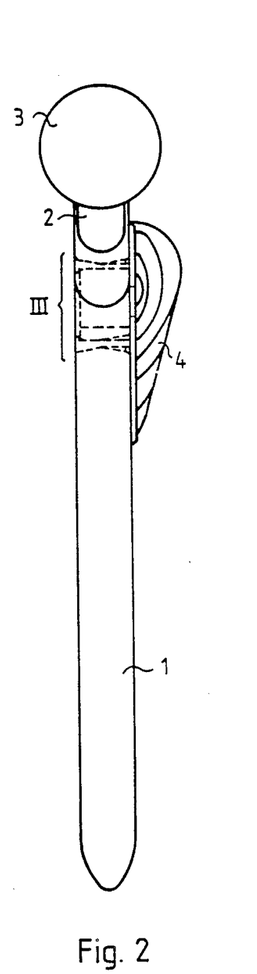
FIG. 2 is a second view of the prosthesis according to FIG. 1.
Figure 4:
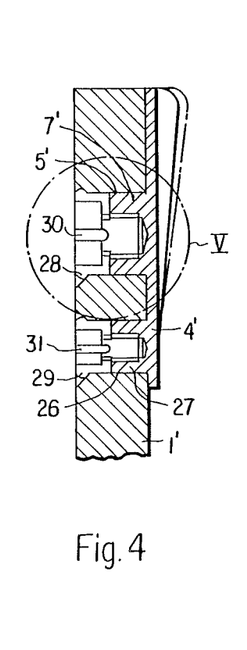
FIG. 4 is a sectional view of a variant of the exemplary embodiment of FIG. 1.
Figure 5:
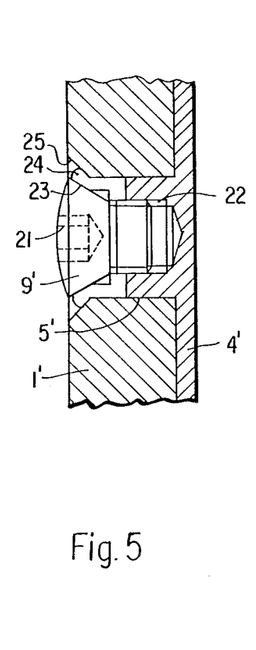
FIG. 5 is an enlarged detail view of the region V of the sectional view of the variant of FIG. 4.

In the exemplary embodiment shown in various views in FIGS. 4–6, as the wedge element a wedge bolt 9' is provided, which has a hexagonal socket 21 with which the bolt can be tightened or loosened using a conventional Allan wrench. The additional element 4' to this end, has a bore with an internal thread 22. Because of the wedge action of the conical underside 23, the upper edge region 24 of the additional element 4' is pressed into a conical recess 25 of the opening embodied as a cylindrical bore 5', so that the edge—which intially protrudes only slightly—is crimped completely over in the manner of a compression rivet and together with the pressing force exerted by the screw 9' holds the additional element firmly.

FIGS. 4 and 6 show that in the exemplary embodiment of the shaft 1 shown, an additional bore 26, which is engaged by a further attachment 27 of the additional part 4', is provided next to the bore 5' to secure against rotation.

The attachments 7' and 27 in this exemplary embodiment are hollow-cylindrical, and a continuous annular bulge 28 and 29 is provided on each respective end, engaging the conical enlargements of the bores 5' and 26 so making it possible simple to snap the attachments into the shaft of the prosthesis. Securing can be done by means of a wedge element, and as shown this element may preferably be embodied as a bolt having a wedge-shaped underside of its head. U-shaped recesses 30 and 31 in the cylindrical elements lend these elements the necessary elasticity.

The concial enlargements of the bores are symmetrical so that an additional element 4', in the particular suitable shaping, can be selectively introduced from either side. The second bore 26 radiably prevents an unintended rotation of the additional element.

The additional element is preferably produced from titanium or some plastic that is compatible with the body. If it is made of metal, then there will be substantially no squeezing deformation of the peripheral region when the wedge bolt is thightened. In this case a continuously cylindrical embodiment of the bores 5' and 26 is favorable. Also, the extension 26 needs to have merely the shape of a cylinder, to present resistance solely to rotation.

Figure 7A:
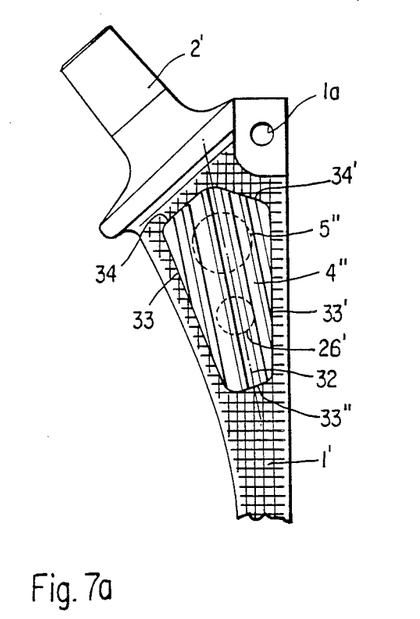
FIGS. 7a, 7b, and 7c are three views of a variant having a symmetrical additional element.
Figure 7B:
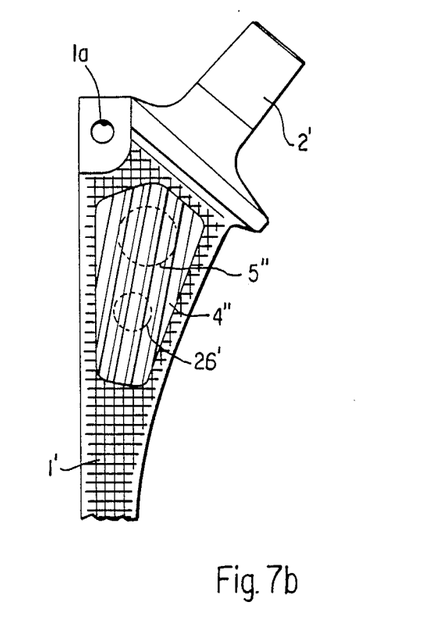
Figure 7C:
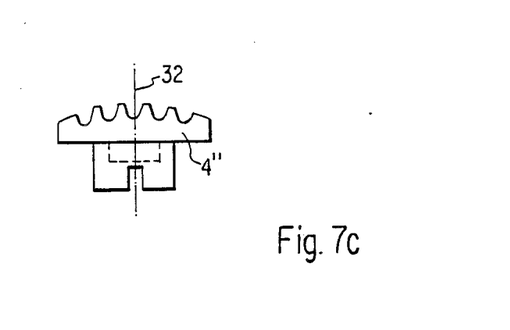

In FIGS. 7a–7c, a further exemplary embodiment of the prosthesis according to the invention is shown, having an additional element 4'', which is symmetrically embodied. The shaft prosthesis 1' having a cone 1'' for receiving an articular head has smooth continuous cylindrical bores as its recesses 5'' and 26', which except for a slight rounding in the vicinity of the transition to the outer surfaces has no additional machined areas.

The additional element 4' is symmetrically embodied with respect to an axis 32 (mirror plane), so that it can be used on both sides. FIGS. 7a, and 7b shown the prosthesis in a view from both sides, with an identical additional element 4'' in the inserted state. The bores 5'' and 26 are located on the axis of symmetry 32.

By insertion into the recesses and fastening with a spreading screw (or similar element, as described in connection with the above exemplary embodiments), the shaft form can be converted into that of a left or right prosthesis by using a single additional element. The physician is thus in a position to produce a prothesis of the desired shape, beginning with a single packaged unit containing the shaft 1' and one additional element 4' as well as associated fastening means.

The additional element 4' has a five-sided basic shape, and the two longest side faces form an angle that substantially corresponds to the angle of the lateral limiting edges 432 and 32', as viewed in the direction of the recesses 5'' and 26' serving for fastening, in the region adjoining these recesses. The axis of symmetry forms the left bisector, and the enlarged region is defined by two symmetrical gable-like edges 34 and 34', which meet at the line of symmetry. Another limiting line extends from each of these gable-like limiting lines 34 and 34', parallel to the prosthesis collar or to the corresponding limiting line of the prosthesis, that is, at right angles to the axis of the fastening cone 2'.

Because of the gable-like five-sided shape of the additional element, one region remains free in the vicinity of one gable-like limiting line (34' in FIG. 7a, and 34 in FIG. 7b), this region presenting an additional opportunity for fastening the prosthesis shaft, for instance by means of a bore 1a. The shape of the additional element is thus generally pentagonal in plan view, and the gable-like sides 34 and 35 are opposed by a narrow limiting side 33', which intersects the line of symmetry 32 at right angles.

In FIG. 7c, the additional element 4" is shown in section. The sectional direction extends at right angles to the plane of symmetry 32. The element 4' is convexly curved and provided with grooves, and the shape of the curvature and of the grooves is also symmetrical to the plane 32. The curvature also has its apex, that is, its highest region, in the vicinity of the section having this plane 32.

Figure 8:
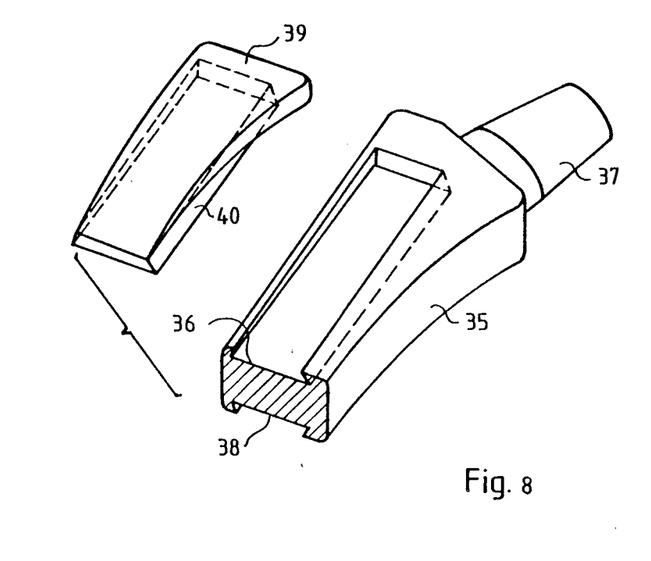
FIG. 8 is a perspective fragmentary view of a further variant of the exemplary embodiment of FIG. 1.
Figure 9:
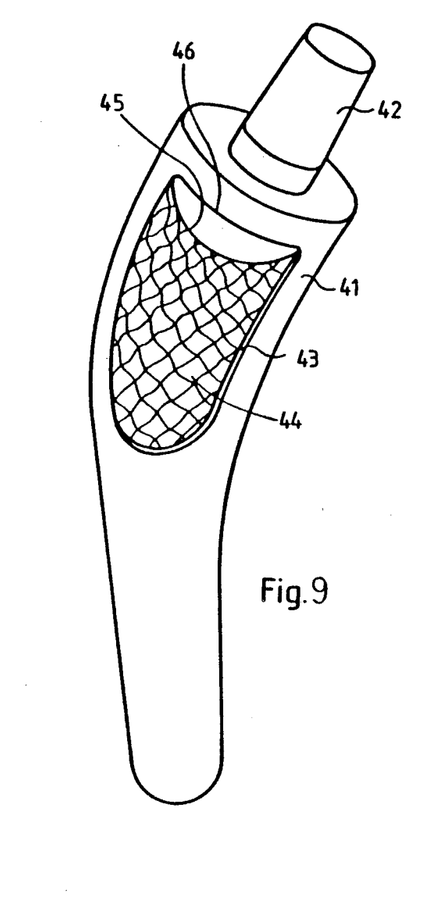
Figure 10A:
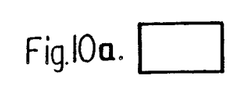
Figure 10B:
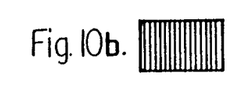
Figure 10C:
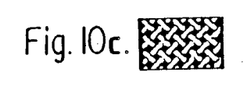
Figure 10D:
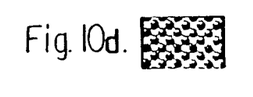

In FIG. 8, a further exemplary embodiment of the implant according to the invention, in the form of a shaft prosthesis, is shown.

Provided in the shaft 35, as the basic element, is a dovetail-like recess 36, which diminishes in depth in the direction toward the end of the shaft facing the cone 37, and with its bottom face intersects the outer face of the contour of the shaft. The recess thus has dovetail-like cross section, which from the shaft end merges along a straight path with the surface of the shaft and penetrates to a greater depth with increasing proximity to the end of the shaft carrying the neck 37. The bottom face of the dovetail-like recess 36 and a recess 38 disposed symmetrically with it on the opposite side of the shaft thus extend parallel to the plane (plane of symmetry) of the shaft in which its greatest curvature is located.

An attachment element 39, as the additional element, has a (positively shaped) dovetail-like attachment 40, which can be pushed into the recess 36. The dovetail-like attachment 40, correspondingly with the recess 36, has a height that diminishes in the opposite direction from the direction of introduction, so that the element 39 in the inserted state rests flush on the surface of the shaft 35 that adjoins the recess 36 on both sides.

An element shaped symmetrically to the element 39 can alternatively be introduced into the recess 39 in a corresponding manner. In this manner, before the shaft is introduced, a left or right prosthesis can be produced by inserting the element 39 or some symmetrically shaped element. The forces brought to bear when the prosthesis shaft is driven in retain the element 39 in its position. A locking pin (not shown) can additionally be provided in the transverse direction to prevent unintentional loosening, the locking pin being introduced after the insertion of the element and for example taking the form of a grooved dowel pin. The arrangement is secured against unintentional loosening during the driving in of the prosthesis shaft by the provision that the additional element is driven in contrary to the driving-in direction of the shaft – that is, the additional element is driven in in the direction of its conical or other enlargement. Because the recess ends blind, a stop is formed that secures the additional element against unintentional loosening during the driving-in process.

The invention is not restricted in its embodiment to the preferred exemplary embodiments described above. Instead, a number of variants that makes use of the provisions described, even with fundamentally different forms, are conceivable.

What is claimed is:

1. A nonmirror-symmetrical bone prosthesis comprising an elongated shaft which is divided into mirror symmetrical anterior and posterior halves about a medial-lateral plane, said halves forming outer anterior and posterior surfaces, respectively, and each of said anterior and posterior surface including an anchoring recess formed therein; and a wedge element having a tapered bone engaging surface and an opposite shaft engaging surface; said shaft engaging surface having anchoring means formed thereon, wherein said wedge is attached to one of said coupling said anchoring means to said recess to form said nonmirror-symmeterical prosthesis that is specific to only one of the bone structure of the right of left side of the body.

2. A bone implant as defined by claim 1, characterized in that shaft the has an outer contour, said recesses forming a continuous surface with said outer contour.

3. A bone implant as defined by claim 2, characterized in that said shaft includes a plane of symmetry dividing said shaft-shaped element into two symmetrical halves, the recess being disposed symmetrically with respect to the plane of symmetry.

4. A bone implant as defined by claim 2, characterized in that the recess is embodied as one of a bore, a slit or a groove extending along the surface of said shaft and open toward said center surfaces thereof.

5. A bone implant as defined by claim 2, characterized in that said recess tapers in the direction toward said outer surface at which said wedge element is joined, and said wedge element includes a retaining element engaging said recess, said retaining element enlarging in the direction toward the shaft.

6. A bone implant as defined by claim 5, characterized in that said retaining element includes elastic, outwardly biased and spreadable extensions.

7. A bone implant as defined by claim 1, characterized in that said recess of said shaft and said wedge element include complementary undercuts, further including retaining elements having protruding means engaging corresponding undercuts of said recess.

8. A bone implant as defined by claim 2, characterized in that said retaining element is a spreading dowel in the form of one of a wedge pin or wedge bolt having one of a concical head.

9. A bone implant as defined by claim 1, charactrized in a second recess in said shaft and a second retaining element engaging said second recess being eccentric with respect to said first recess.

10. A bone implant as defined by claim 1, characterized in that said wedge element is resilient.

11. A bone implant as defined by claim 1, characterized in that said wedge element includes a sheet-metal member defining a cavity with said shaft.

12. A bone implant as defined by claim 11, characterized in that the cavity has as access opening.

13. A bone implant as defined by claim 12, characterized in that a portion of said sheet metal member is spaced from said shaft forming said access opening.

14. A bone implant as defined by claim 1, characterized in that said shaft has a surface structure containing regions taken from the class consisting of rib-like, madrepric and porous depressions promoting connection thereof with an adjoining bone region, and resorbable material filling said depressions whereby, after the implantation, the resorable material is replaced by bone material.

15. A system for a bone implant as defined by claim 1, characterized in that a plurality of said wedge elements, each wedge element having fastening elements of identical shapes, said fastening elementing differing in at least one of size, resiliency and surface structure.

16. A bone implant as defined by claim 1, characterized in that said shaft includes longitudinal ribs at the outer surface thereof, said longitudinal ribs at the outer surface extending parallel to the plane of symmetry thereof.

* * * * *

UNITED STATES PATENT AND TRADEMARK OFFICE
CERTIFICATE OF CORRECTION

PATENT NO. : 4,842,606

DATED : June 27, 1989

INVENTOR(S) : Curt KRANZ, et al.

It is certified that error appears in the above-identified patent and that said Letters Patent is hereby corrected as shown below:

Claim 1 should read as follows:

Column 8, line 2, after "said", first occurrence, insert --anterior or posterior surface and fixed thereto by--; line 5, change "of", second occurrence, to --or--.

Signed and Sealed this

Second Day of October, 1990

Attest:

HARRY F. MANBECK, JR.

*Attesting Officer*     *Commissioner of Patents and Trademarks*

UNITED STATES PATENT AND TRADEMARK OFFICE
CERTIFICATE OF CORRECTION

PATENT NO. : 4,842,606

DATED : June 27, 1989

INVENTOR(S) : KRANZ et al.

It is certified that error appears in the above-identified patent and that said Letters Patent is hereby corrected as shown below:

Column 1, Line 42, should read:

> having an additional element attached to it is not restricted, either. If the fastening means for two differential additional elements are disposed symmetri- Signed and Sealed this Sixth Day of July, 1993

*Attest:*

MICHAEL K. KIRK

*Attesting Officer*     *Acting Commissioner of Patents and Trademarks*